(12) United States Patent
Golitz

(10) Patent No.: US 7,655,473 B2
(45) Date of Patent: Feb. 2, 2010

(54) METHOD AND DEVICE FOR DETERMINING THE CONCENTRATION OF NITRITE

(75) Inventor: Andreas Golitz, Moers (DE)

(73) Assignee: Hach Lange GmbH, Berlin (DE)

( * ) Notice: Subject to any disclaimer, the term of this patent is extended or adjusted under 35 U.S.C. 154(b) by 225 days.

(21) Appl. No.: 11/884,514

(22) PCT Filed: Feb. 13, 2006

(86) PCT No.: PCT/EP2006/050885

§ 371 (c)(1),
(2), (4) Date: Aug. 16, 2007

(87) PCT Pub. No.: WO2006/087311

PCT Pub. Date: Aug. 24, 2006

(65) Prior Publication Data

US 2008/0194033 A1 Aug. 14, 2008

(30) Foreign Application Priority Data

Feb. 17, 2005 (DE) .......................... 10 2005 007 142

(51) Int. Cl.
*G01N 33/00* (2006.01)
*G01N 35/10* (2006.01)
*B01J 19/00* (2006.01)

(52) U.S. Cl. .................. 436/110; 436/106; 436/43; 422/63; 422/68.1

(58) Field of Classification Search ............ 436/10, 436/43, 110, 106; 422/63, 68.1; 204/157.15
See application file for complete search history.

(56) References Cited

U.S. PATENT DOCUMENTS

| 4,412,006 A | 10/1983 | Cox et al. |
| 5,300,441 A | 4/1994 | Fujinari et al. |
| 5,630,987 A | 5/1997 | Briggs et al. |
| 5,858,792 A | 1/1999 | Fanning et al. |
| 5,871,620 A * | 2/1999 | Haug et al. ............ 204/157.15 |

FOREIGN PATENT DOCUMENTS

| DE | 33 24 606 | 1/1985 |
| DE | 199 02 396 | 8/2000 |
| JP | 2005-164289 | 6/2005 |
| WO | WO 97/35191 | 9/1997 |

OTHER PUBLICATIONS

Machine Translation of DE 199 02 396. Meuller et al., Process for measuring the nitrate content of drinking water uses a wavelength inducing an absorption maximum and an absorption minimum of the nitrate concentration curve.*

(Continued)

*Primary Examiner*—Walter D Griffin
*Assistant Examiner*—Christine T Mui
(74) *Attorney, Agent, or Firm*—Fay Sharpe LLP

(57) ABSTRACT

A method for automatically determining the concentration of nitrite in a liquid sample includes:
  determination of the extinction of the liquid sample at a wavelength $\lambda$ of 150-250 nm,
  addition of a nitrite reducing agent to the liquid sample,
  determination of the extinction of the reduced liquid sample at a wavelength $\lambda$ of 150-250 nm, and
  determination of the nitrite concentration from the difference between the concentration values obtained from the extinctions of the non-reduced and the reduced liquid samples.

14 Claims, 3 Drawing Sheets

OTHER PUBLICATIONS

Vogel J et al: "Nitrate determination in natural waters by spectral photometry with a miniaturized fiber-coupled flow cell", Second European Workshop on Optical Fibre Sensors, Jun. 9-11, 2004, Santander, Spain, Bd. 5502, Nr. 1, 2004, Seiten 402-405.

* cited by examiner

ABSTRACT# METHOD AND DEVICE FOR DETERMINING THE CONCENTRATION OF NITRITE

BACKGROUND

The invention relates to a method and a device for automatically determining the concentration of nitrite in a liquid sample.

Such methods and devices are employed, inter alia, in waste water clarification plants for monitoring and controlling the clarifications process. In the known measuring methods and devices, the extinction of the liquid sample of the waste water is determined with the aid of UV radiation. Using the extinction value obtained in this manner, the concentration of the sum of nitrite and nitrate is calculated. Since the spectral curve shapes of the extinction of nitrite and nitrate show large similarities, photometric means virtually do not allow for an exact differentiated determination of nitrite or nitrate in a liquid sample containing both nitrite and nitrate. However, monitoring or controlling the correct process of nitrification, i.e. the microbiological oxidation of ammonium over nitrite using Nitrosomonas, and the subsequent microbiological oxidation of nitrite to nitrate using Nitrobacter, requires individual determination of both the concentration of nitrite and the concentration of nitrate.

It is thus an object of the invention to provide a method and a device for automatically determining the concentration of nitrite in a liquid sample possibly containing nitrate.

SUMMARY

The method for automatically determining the concentration of nitrite in a liquid sample according to one aspect comprises the following method steps:
- determination of the extinction of the liquid sample at a wavelength λ of 150-250 nm,
- addition of a nitrite reducing agent to the liquid sample,
- determination of the extinction of the reduced liquid sample at a wavelength λ of 150-250 nm, and
- determination of the nitrite concentration from the difference between the extinctions of the non-reduced and the reduced liquid sample.

During the first extinction determination step, the concentration of the sum of nitrite and nitrate in the liquid sample is determined with the aid of the UV photometry, as is known from prior art. Subsequently, an adequate amount of a nitrite reducing agent is added to the liquid sample, i.e. in a amount at which a complete nitrite reduction takes place. Thereby the nitrite is completely expelled as nitrogen from the liquid sample.

Preferably, this process also allows the nitrate concentration to be determined on the basis of the extinction determination of the reduced liquid sample. The reduced liquid sample does no longer contain nitrite, but exclusively contains nitrate. Therefore the extinction determination of the reduced liquid sample shows the concentration of nitrate in the liquid sample.

Generally, different nitrite reducing agents can be used for reducing purposes, for example ammonia, hydrazoic acid, urea, amidosulphuric acid, etc. Preferably, amidosulphuric acid is used as a nitrite reducing agent since said acid does not show any self-extinction in the monitored spectrum, is not volatile, is not explosive, and is relatively stable. Amidosulphuric acid is thus suitable particularly in an automatic process where the nitrite reducing agent must be stored in a storage tank for an extended period of time.

Preferably, the liquid sample is mixed in a suitable mixer after the addition of the nitrite reducing agent. Thereby the reduction of the nitrite is accelerated, and a homogeneous mixing of the liquid sample with the nitrite reducing agent is reliably ensured. Preferably, the photometric determination of the extinction takes place at wavelengths λ=213 nm and λ=223 nm. Two measurements at different wavelengths differentiate between nitrate and/or nitrite, and other substances. The spectrum of nitrite and nitrate shows its largest upward slope between approximately λ=210 nm and λ=230 nm. Two measurements in the region of this upward slope allow for a reliable differentiation between nitrite and nitrate, and other substances which are photometrically active in this region.

The determination device according to one aspect for automatically determining nitrite in a liquid sample comprises a measuring chamber for receiving the liquid sample, a sample transporting device for supplying and discharging the liquid sample to and from the measuring chamber, a photometer for determining the extinction of the liquid sample in the measuring chamber, and a reducing agent adding device for feeding the nitrite reducing agent to the measuring chamber. By provision of the reducing agent adding device, a nitrite reducing agent can automatically be added to the liquid sample in the measuring chamber subsequent to the first extinction determination step, said nitrite reducing agent fully expelling the nitrite from the liquid sample. The determination device thus allows the described process for determining nitrite in a liquid sample to be carried out automatically.

According to a preferred embodiment, the measuring chamber is defined by a pivoting fork movable in a gap, and the gap walls, wherein the pivoting fork is adapted to be pivoted out of the gap for the purpose of receiving a new liquid sample. The pivoting fork comprises two fork arms defining an open space between said arms which extends perpendicularly to the base plane of the pivoting fork. The fork arms may be unconnected with each other at their free arm ends, but may also be connected with each other such that they define a closed ring around the measuring chamber. The two sides extending perpendicularly to the base plane of the pivoting fork are defined by the opposing fixed gap walls. This measuring chamber structure is particularly suitable for determination devices configured as immersion probes which are adapted to be directly immersed into a clarification basin for the purpose of continuously determining the concentration of nitrite and nitrate.

When the pivoting fork is pivoted out of the gap, the moving ambient liquid causes the liquid sample surrounded by the pivoting fork to be automatically exchanged for a new liquid sample, said new liquid sample being isolated in the measuring chamber when the pivoting fork is pivoted back into the gap. Thus pumps susceptible to malfunction are not required for supplying and discharging a liquid sample.

Preferably, the two opposing gap walls each comprise a photometer window of quartz glass. The distance between the two photometer windows is the measuring length. The measuring radiation enters into the measuring chamber through the one photometer window, wherein the liquid sample partially absorbs the measuring radiation depending on the constituents in the liquid sample. The measuring radiation leaves the measuring chamber through the opposing photometer window, and impinges onto a wavelength-selective receiver of the photometer which determines the extinction in a wavelength-selective manner, e.g. for two different wavelengths in the UV range.

Preferably, the pivoting fork comprises a mixing tongue which is elastically movable relative to the pivoting fork. The mixing tongue is adapted to be deflected and moved relative to the pivoting fork by its inertia and/or by suitable snap-in elements arranged at the gap walls. Relatively small movements of the pivoting fork after the addition of the nitrite reducing agent cause the liquid sample to be rapidly mixed by the moving mixing tongue, and the nitrite in the overall volume of the liquid sample to be quickly expelled. In this manner, the concentration of nitrite can be quickly determined, and a high measuring frequency, i.e. a rapid measuring sequence, is ensured.

According to a preferred embodiment, the windows are arranged in the base plane of the gap walls, and the pivoting fork cleans the windows while moving past them. Each time the pivoting fork receives a new liquid sample, it cleans the two optical windows, thus ensuring that the windows are clean during the next extinction determination step, and that the determination can be carried out in a trouble-free and faultless manner. The pivoting fork is made from a relatively soft material, e.g. a plastic material, which does not scratch the windows, but cleans them without leaving any residues.

Preferably, the pivoting range of the pivoting fork is shielded by a liquid-permeable cage. Thus larger particles of the liquid are prevented for entering into the pivoting range such that it is nearly precluded that the pivoting fork gets damaged or jammed in the gap.

Alternatively or additionally, the pivoting fork, in its pivoted-out sample exchange position, may be arranged in an open gap defined by two gap walls, said gap preventing to a large extent larger solid particles from entering into the interspace defined by the fork.

Preferably, the device for automatic determination is configured as an immersion probe which may be directly and permanently arranged in a liquid tank, such as a clarification basin.

BRIEF DESCRIPTION OF THE DRAWINGS

An embodiment of the invention will now be described in greater detail with reference to the drawings. The drawings are presented for illustrative purposes and are not to be taken as limiting the claims.

DETAILED DESCRIPTION

Figure 1:
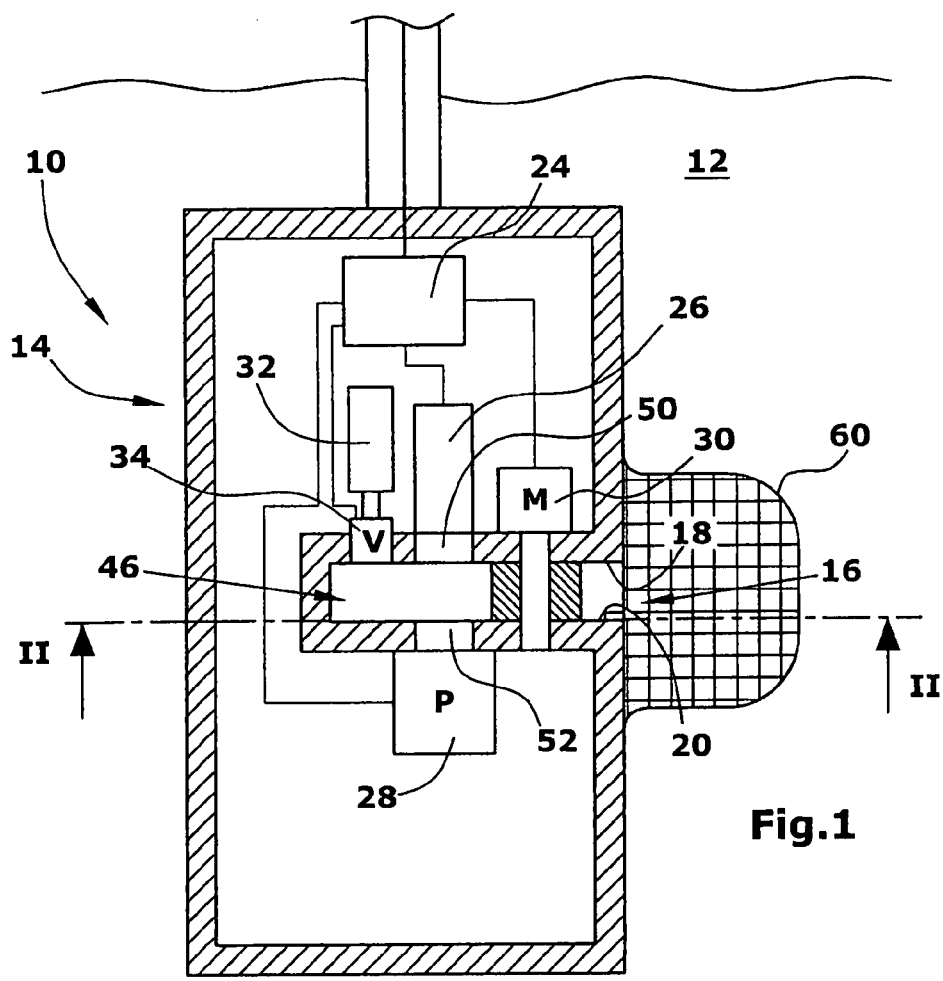
FIG. 1 shows a longitudinal section of a determination device according to one embodiment of the invention configured as an immersion probe.

FIG. 1 shows a determination device 10 configured as an immersion probe which is immersed into a liquid 12. The liquid 12 is waste water in a clarification basin. The determination device 10 serves for quasi-continuous monitoring of the nitrite and the nitrate content in the liquid 12.

The determination device 10 comprises a housing 14 which is essentially configured as an upright cylinder and comprises a gap 16 located in the cylinder transverse plane and approximately in center of the cylinder, said gap 16 being defined by an upper gap wall 18, a lower gap wall 20 and a gap side wall 22. The housing 14 of the determination device 10 is made from metal.

Figure 2:
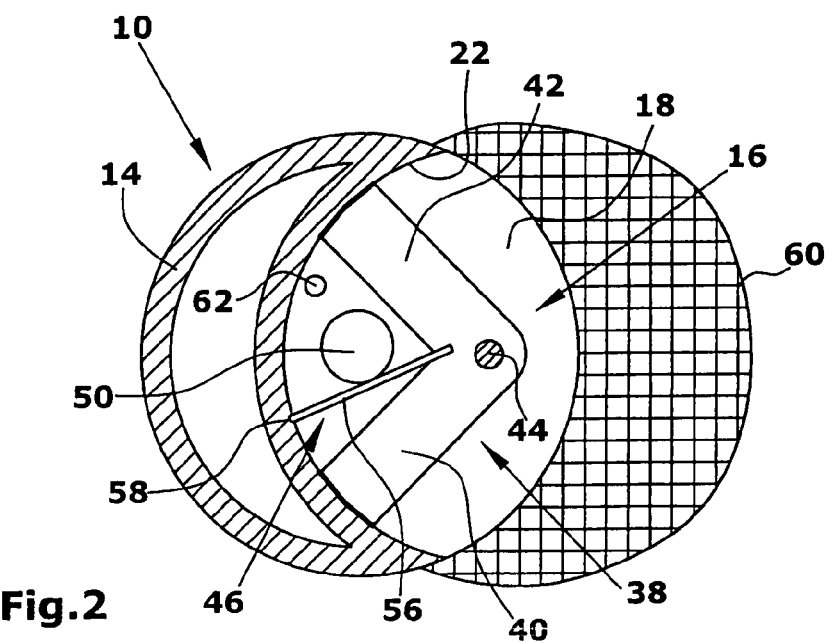
FIG. 2 shows a cross section of the determination device of FIG. 1 with the pivoting fork pivoted back into the gap.

In the housing 14 a control device 24, a UV light source 26, a photometer 28, a pivoting fork pivot motor 30 and a reducing agent adding device composed of a reducing agent tank 32 and a reducing agent valve 34 are arranged. In the gap 16 a pivoting fork 38 defining a sample transporting device is pivotably supported. The pivoting fork 38 comprises two fork arms 40,42 which are arranged at an angle of approximately 80° relative to each other. The pivoting fork 38 is pivotably supported in a transverse plane, i.e. the slot plane, by a shaft 44 driven by the pivot motor 30. In FIG. 2 the pivoting fork 38 is shown in the measuring position, i.e. pivoted into the gap 16, and in FIG. 3 the pivoting fork 38 is shown in the sample exchange position, i.e. pivoted out of the gap 16.

The two arms 40,42 of the pivoting fork 38 and the three walls 18,20,22 of the gap 16 define a measuring chamber 46.

The two opposing gap walls 18,20 each comprise windows 50,52 of quartz glass. The windows 50,52 are arranged in the plane of the two opposing gap walls 18,20, and define the measuring chamber 46 when the pivoting fork 38 is in the measuring position shown in FIG. 2. In the region of the root of the pivoting fork 38 a resilient mixing tongue 56 is arranged which has a slightly larger radial length than the two arms 40,42 of the pivoting fork 38. During a pivoting movement of the pivoting fork 38, the mixing tongue 56 snaps into a snap-in recess 58 provided in the region of the gap wall 22. It is also possible to provide a plurality of snap-in recesses.

The disclosure has been described with reference to an exemplary embodiment. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

In the upper gap wall 20 a reducing agent inlet opening 62 is provided through which the reducing agent is supplied from the reducing agent tank 32 to the measuring chamber 46 via the reducing agent valve 34. Alternatively or additionally to the reducing agent valve 34, a microdosing pump may be provided.

The pivoting fork 38 is made from a plastic material and has such a height that no interspace remains between the pivoting fork 38 and the walls 18,20, 22 of the gap 16 through which the liquid sample can flow out of the measuring chamber 46, such that the arms 40,42 of the pivoting fork 38 wipe the gap walls 18,20. Since the two windows 50,52 are arranged in the plane of the respective walls 18,20 of the gap 16, the two windows 50,52 are also wiped and cleaned during each pivoting movement of the pivoting fork 38. The same may apply to the mixing tongue 56.

On the outside of the housing 14 a liquid-permeable metal cage 60 shielding the pivoting range of the pivoting fork 38 is provided. The cage 60 may be made of a closed-meshed wire mesh, or the like. The cage 60 prevents larger solid particles from entering into the pivoting range of the pivoting fork 38. In this manner, a high mechanical operational safety is ensured since it is nearly precluded that the pivoting fork 38 gets jammed in the gap 16.

Figure 3:
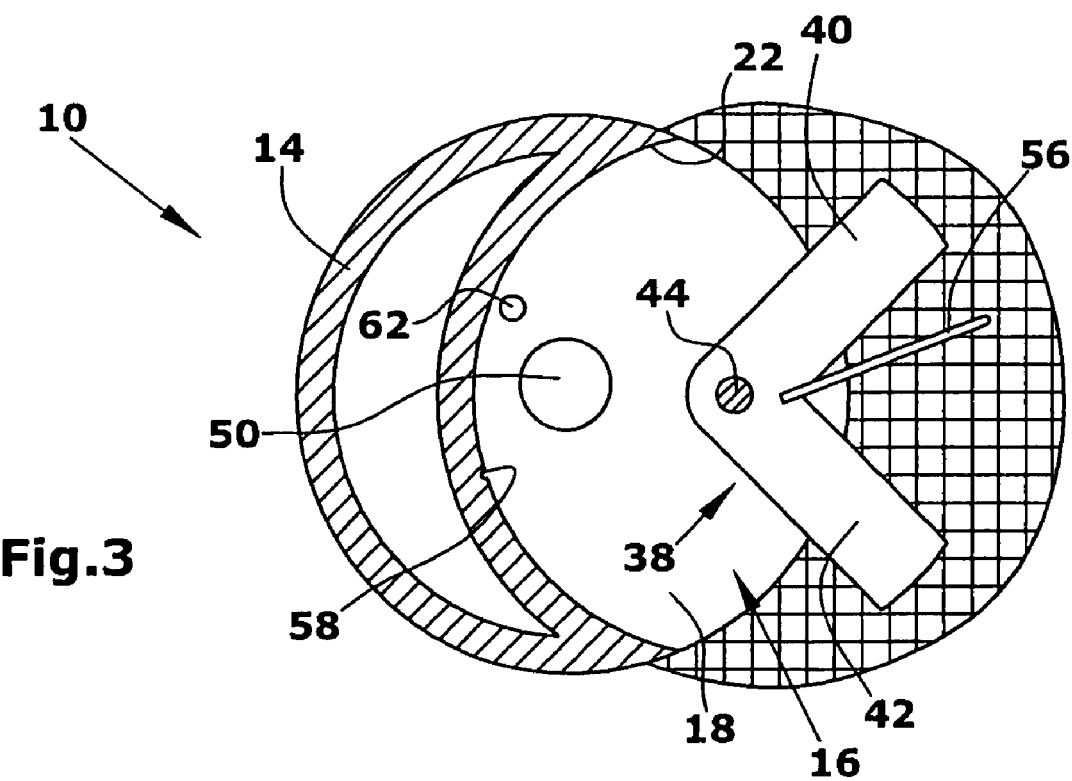
FIG. 3 shows the determination device of FIG. 2 with the pivoting fork pivoted out of the gap.

A measuring process is performed as follows:

First, the pivoting fork 38 is pivoted out of the gap 16, as shown in FIG. 3, and is subsequently pivoted back into the gap 16, as shown in FIG. 2. In this manner, a liquid sample is supplied to the measuring chamber 46. Now a first photometric determination of the extinction of the liquid sample is carried out, namely at the wavelengths $\lambda=213$ nm and $\lambda=223$ nm. On this basis, the concentration of the sum of nitrite and nitrate in the liquid sample is calculated.

Now the reducing agent valve 34 is opened, and a defined amount of reducing agent is supplied to the measuring chamber 46 via the opening 62. By slightly pivoting the pivoting fork 38, the mixing tongue 56 is set into movement relative to the pivoting fork 38, and the supplied reducing agent is thus mixed with the liquid sample.

Amidosulphuric acid is used as the reducing agent. Nitrite can be expelled from the liquid sample according to the following chemical equation:

$$HNO_2 + (NH_2)HSO_3 \rightarrow N_2 + H_2SO_4 + H_2O$$

The gap height is 1-2 mm such that the measuring chamber volume ranges approximately between 1 ml and 10 ml. An amount of less than 10 µl of the reducing agent is added.

The reducing agent completely expels the nitrite from the liquid sample within a few seconds. Subsequently, a second photometric determination of the extinction of the liquid sample at the same wavelengths as stated above is carried out, and the nitrate concentration is determined from the measured extinction values. Then the nitrite concentration is obtained from the difference between the sum extinction measured first and the nitrite concentration.

With the aid of the described process, the concentration of both nitrite and nitrate in a liquid sample can be exactly determined.

Figure 4:
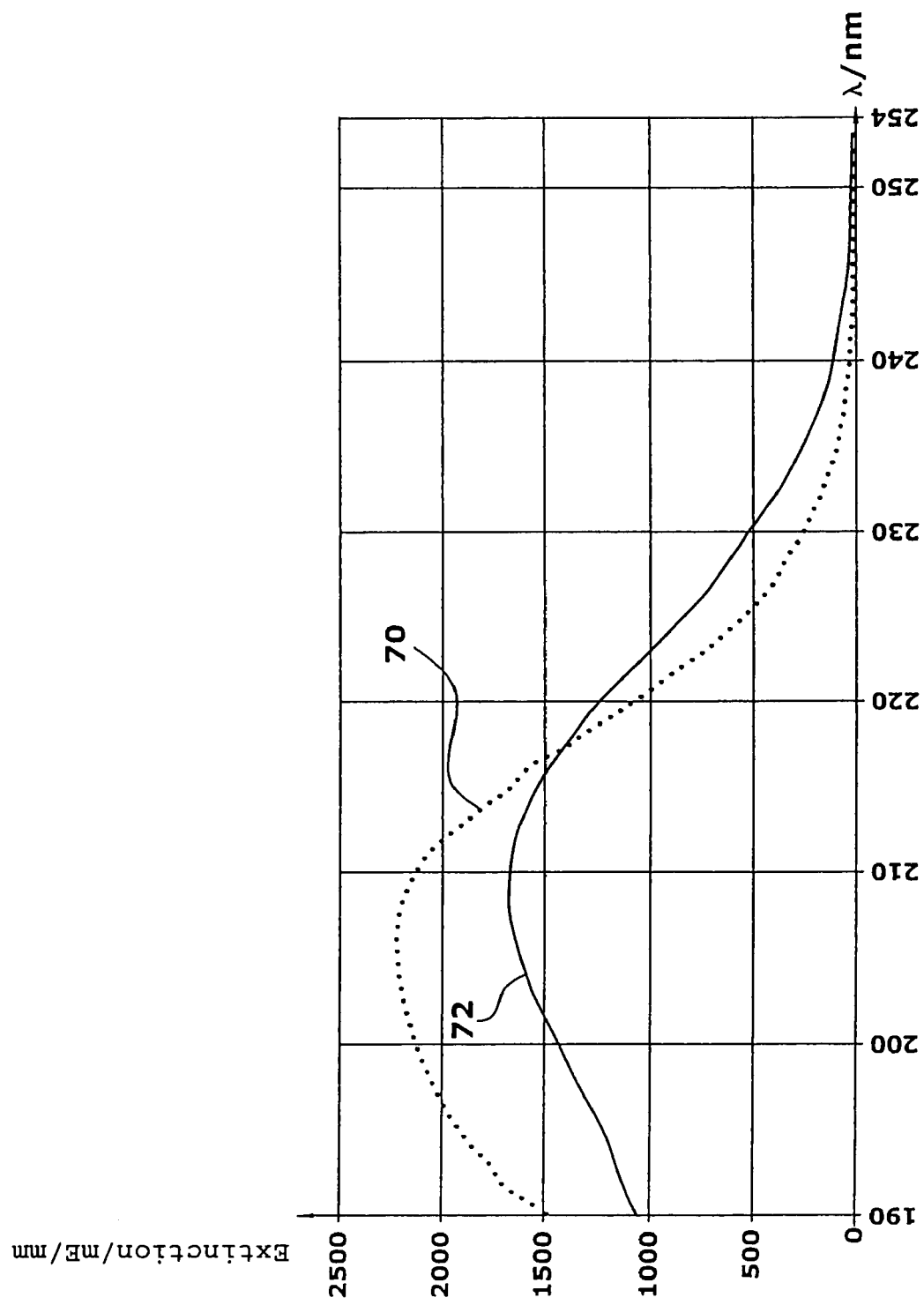
FIG. 4 shows a graphic representation of the extinction spectrum of nitrite and nitrate in the UV range.

FIG. 4 shows a nitrate extinction curve 70 and a nitrite extinction curve 72. As can be seen, the maxima of the two curves are spectrally very close to each other, and the two curves 70,72 show only a very small extinction or no extinction at all above 240 nm. This indicates that the photometric extinction determination alone does not allow for a differentiation or allows only for a very inaccurate differentiation between the concentrations of nitrate and nitrite.

The invention claimed is:

1. A determination device for automatically determining the concentration of nitrite in a liquid sample comprising:
    a measuring chamber for receiving the liquid sample, the measuring chamber being defined by a pivoting fork moved in a gap, and by walls of said gap,
    a photometer for determining the extinction of said liquid sample in said measuring chamber,
    a sample transporting device for supplying and discharging said liquid sample to and from said measuring chamber, wherein said pivoting fork is adapted to be pivoted out of said gap for the purpose of receiving a new liquid sample, and forms part of the sample transporting device, and
    a reducing agent adding device for feeding a reducing agent into said measuring chamber.

2. The determination device according to claim 1, wherein the walls are oppositely disposed and each comprises an optical window.

3. The determination device according to claim 1, wherein the pivoting fork comprises a mixing tongue which is movable relative to arms of said pivoting fork.

4. The determination device according to claim 2, wherein the windows are arranged in a base plane of the gap walls, and the pivoting fork cleans said windows while being pivoted past them.

5. The determination device according to claim 1, wherein the pivoting fork has a pivoting range and is shielded by a liquid-permeable cage.

6. The determination device according to claim 1, wherein said determination device is configured as an immersion probe.

7. A method for automatically determining the concentration of nitrite in a liquid sample in a sample chamber, the sample chamber being defined by a pivotable fork and adjoining wall surfaces, the method comprising:
    prior to determining an extinction of the liquid sample, pivoting the fork to capture the liquid sample,
    determining of the extinction of the liquid sample at a wavelength $\lambda$ of 150-250 nm,
    adding of a nitrite reducing agent to said liquid sample,
    determining of the extinction of the reduced liquid sample at a wavelength $\lambda$ of 150-250 nm, and
    determining of a nitrite concentration from a difference between concentration values obtained from the extinctions of the non-reduced and the reduced liquid samples.

8. The method according to claim 7 wherein the adjoining wall surfaces include windows through which light of the 150-250 nm wavelength passes and the method further includes:
    cleaning the windows as the fork pivots past them.

9. The method according to claim 8 wherein a mixing tongue is mounted to the pivoting fork for movement therewith and the method further includes:
    after adding the nitrate reducing agent to the liquid sample, mixing the sample and the nitrate reducing agent.

10. The method according to claim 7, wherein the reducing agent is amidosulphuric acid.

11. The method according to claim 7, wherein the nitrate concentration is obtained from the extinction of the reduced sample.

12. The method according to claim 7, wherein the liquid sample is mixed prior to the extinction determination of the reduced liquid sample.

13. The method according to claim 7, wherein the extinction determination of the liquid samples is carried out at the wavelengths $\lambda=213$ nm and $\lambda=223$ nm.

14. A device for automatically determining the concentration of nitrite in a liquid sample, the device comprising:
    a sample chamber for holding the liquid sample, the sample chamber including walls that define a gap and a pivoting fork mounted to pivot in the gap,
    means for determining the extinction of the liquid sample in the sample chamber at a wavelength $\lambda$ of 150-250 nm,
    means for adding a nitrite reducing agent to said liquid sample in the sample chamber,
    means for determining the extinction of the reduced liquid sample at a wavelength $\lambda$ of 150-250 nm, and
    means for determining a nitrite concentration from a difference between concentration values obtained from the determined extinctions of the non-reduced and the reduced liquid samples.

* * * * *